(12) United States Patent
Heath et al.

(10) Patent No.: US 11,116,457 B2
(45) Date of Patent: Sep. 14, 2021

(54) DETECTOR ALIGNMENT ASSEMBLY AND METHOD

(71) Applicant: CARESTREAM HEALTH, INC., Rochester, NY (US)

(72) Inventors: Michael D. Heath, Rochester, NY (US); Xiaohui Wang, Pittsford, NY (US)

(73) Assignee: Carestream Health, Inc., Rochester, NY (US)

(*) Notice: Subject to any disclaimer, the term of this patent is extended or adjusted under 35 U.S.C. 154(b) by 0 days.

(21) Appl. No.: 16/486,909

(22) PCT Filed: Mar. 6, 2018

(86) PCT No.: PCT/US2018/021006
§ 371 (c)(1),
(2) Date: Aug. 19, 2019

(87) PCT Pub. No.: WO2018/165066
PCT Pub. Date: Sep. 13, 2018

(65) Prior Publication Data
US 2019/0380665 A1     Dec. 19, 2019

Related U.S. Application Data (60) Provisional application No. 62/467,856, filed on Mar. 7, 2017.

(51) Int. Cl.
*A61B 6/00* (2006.01)
*A61B 6/08* (2006.01)

(52) U.S. Cl.
CPC .............. *A61B 6/08* (2013.01); *A61B 6/587* (2013.01); *A61B 6/4405* (2013.01)

(58) Field of Classification Search
None
See application file for complete search history.

(56) References Cited

U.S. PATENT DOCUMENTS

| | | | |
|---|---|---|---|
| 4,836,671 A * | 6/1989 | Bautista | A61B 6/08 250/491.1 |
| 5,729,475 A | 3/1998 | Romanik, Jr. | |
| 7,954,719 B2 * | 6/2011 | Zhu | G06K 7/10544 235/462.42 |
| 8,568,028 B2 | 10/2013 | Wendlandt et al. | |
| 8,821,015 B2 | 9/2014 | Stagnitto et al. | |
| 2006/0109958 A1 | 5/2006 | Ertel et al. | |
| 2011/0164728 A1 | 7/2011 | Tsuchiya et al. | |
| 2012/0039447 A1 * | 2/2012 | Lalena | A61B 6/4208 378/206 |
| 2016/0135764 A1 | 5/2016 | Wojcik et al. | |

FOREIGN PATENT DOCUMENTS

WO     2014/173741     10/2014

OTHER PUBLICATIONS

International Search Report dated May 18, 2018 for International Application No. PCT/US2018/021006, 3 pages.

* cited by examiner

*Primary Examiner* — Hoon K Song (57) ABSTRACT

Laser sources are configured to project planar laser beams in a preselected geometric relationship. A laser detector is configured to detect, locate, and identify the planar laser beams.

17 Claims, 7 Drawing Sheets

DETECTOR ALIGNMENT ASSEMBLY AND METHOD

CROSS REFERENCE TO RELATED APPLICATIONS

This application claims the benefit of and is a U.S. National Phase filing of PCT Application PCT/US2018/021006 filed Mar. 6, 2018 entitled "DETECTOR ALIGNMENT ASSEMBLY AND METHOD", in the name of Michael D. Heath et al., which claims benefit of U.S. Patent Application Ser. No. 62/467,856, filed Mar. 7, 2017, in the name of Michael D. Heath et al., and entitled DETECTOR ALIGNMENT ASSEMBLY.

BACKGROUND OF THE INVENTION

The subject matter disclosed herein relates to mobile radiographic imaging, and in particular to a device that projects detectable laser beams used to measure alignment between a digital radiographic (DR) detector and an x-ray radiation source.

One embodiment of a mobile radiographic imaging system uses an x-ray source assembly attached to a support arm which, in turn, is attached to a transportable base such as a wheeled base having motor driven wheels, or a transportable base without motor driven wheels that is light enough to be manually maneuvered within a medical facility. U.S. Pat. No. 8,568,028 discloses one such exemplary mobile radiographic imaging system and is hereby incorporated by reference herein in its entirety. Such a portable imaging system may use a DR detector positioned on one side of a patient while the x-ray source is positioned in a complimentary location, on an opposite side of the patient, by manipulating the x-ray source assembly attached to the support arm. An exemplary method and apparatus for achieving a proper alignment between an x-ray source in a mobile radiographic imaging system and a DR detector is disclosed in U.S. Pat. No. 8,821,015, which is hereby incorporated by reference herein in its entirety. An exemplary x-ray source assembly may include a standard x-ray tube head, a plurality of individual distributed CNT sources, a moving monoblock x-ray source, one or more collimator blades, or a combination thereof, among other components.

The discussion above is merely provided for general background information and is not intended to be used as an aid in determining the scope of the claimed subject matter.

BRIEF DESCRIPTION OF THE INVENTION

One critical aspect of mobile radiographic imaging is alignment of the x-ray source and a wireless DR detector used to capture radiographic images. One solution to achieve alignment may entail measuring a difference in spatial position and orientation between two coordinate systems, or two frames of reference—one for the radiographic detector and one for the x-ray source. Each frame of reference may use a three-variable xyz coordinate system, for example. Thus, properly aligning the x-ray source and the digital detector may be defined as reconciling six degrees of freedom. The spatial coordinates for the x-ray source focal spot for each projection image in a radiographic capture sequence relative to the detector needs to be known in order to accurately process radiographic images, in particular, reconstructing a 3D image from a plurality of captured 2D projection images using a reconstruction algorithm. In addition to knowing the capture geometry of the source and detector, another aspect of the imaging geometry may include avoidance of overfilling an area of the detector with x-rays.

A mobile radiographic imaging system may include a tomosynthesis system that provides a technologist with (1) feedback to enable the technologist to manually position an x-ray tubehead relative to a detector within a specified tolerance of the correct position; and (2) imaging geometry data, such as focal spot positions relative to the detector, for tomosynthesis reconstruction as described above. The mobile radiographic imaging system may also be used for x-ray source and grid alignment. One approach to achieving an alignment within specified tolerances includes defining frames of reference using one coordinate system for the x-ray head and another for the detector. The geometric relationship between the coordinate systems may then be determined using a coordinate transformation, and may be adjusted by manual or automatic translation and/or rotation of the detector and/or x-ray head. Once established, this coordinate transformation may be used to compute the position and orientation of any structure on the x-ray head relative to the detector frame of reference. These x-ray head structures may include individual ones of distributed CNT sources, a moving monoblock x-ray source at a moment in time, a standard tube head, one or more collimator blades, or an anode surface position.

As disclosed herein, a DR detector may be positioned in a fixed spatial relationship to laser sources that are configured to project planar laser beams having detectable linear dimensions. One or more laser detectors may be configured to detect and identify the planar laser beams along their linear dimensions.

In one embodiment, a first source of electromagnetic radiation is configured to project a first planar beam detectable along a first linear dimension, and a second source of electromagnetic radiation configured to project a second planar beam detectable along a second linear dimension. The first and second sources are fixed in positions such that their planar beams intersect linear detectors.

In another embodiment, a system having first and second sources of electromagnetic radiation each configured to project planar beams having detectable linear dimensions includes a detector configured to detect the planar beams each at separate positions along their respective linear dimensions.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This application claims priority to U.S. Patent Application Ser. No. 62/467,856, filed Mar. 7, 2017, in the name of Heath et al., and entitled DETECTOR ALIGNMENT ASSEMBLY, which is hereby incorporated by reference herein in its entirety.

Figure 1:
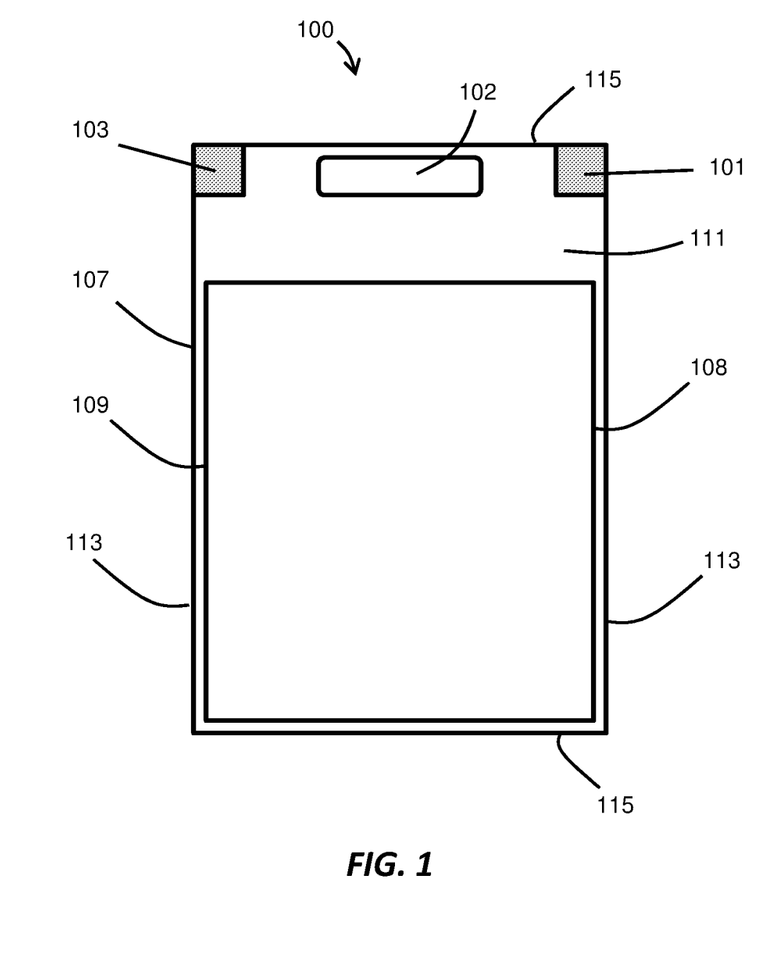
FIG. 1 is a schematic diagram of a detector alignment assembly that contains a digital radiographic detector and a pair of laser modules.

FIG. 1 illustrates a detector assembly 100 which may include a generally planar panel-shaped housing 107 having a detector 109 comprising several layers positioned in an interior region of the housing 107, which detector assembly 100 may be manually carried by using a handle opening 102 in the housing 107. The housing 107 may be said to have parallel lengthwise edges 113 each perpendicular to two parallel widthwise edges 115. The detector 109 may be formed as described in U.S. Patent Application Publication US 2016/0135764 A1, entitled TILED DIGITAL RADIOGRAPHY DETECTORS FOR LONG-LENGTH IMAGING, which description corresponding to FIGS. 1-4 therein is hereby incorporated by reference herein. In one embodiment, the housing 107 may be capable of receiving and securing a standalone detector 109 within a rectangular recess 108 of the housing 107 which may be manually carried by using a handle opening 102 in the housing 107. The detector assembly 100 includes a first commercially available laser module 101 that emits a planar laser beam, which may be referred to as a uniform laser line module 101. The detector assembly 100 also includes a second commercially available laser module 103 that emits planar cross beams, which may be referred to as a laser cross line module 103. The laser line module 101 may be configured to emit a planar laser beam that is detectable along a linear length in one dimension. The cross line module 103 may be configured to emit two intersecting planar laser beams that are each detectable along linear lengths in two different dimensions. The laser modules 101, 103, emit their respective planar laser beams in a direction away from a top surface 111 of the detector assembly 100 toward the viewer of FIG. 1. Although the laser modules 101, 103, are shown to be positioned at opposite upper corners of the housing 107, the laser modules 101, 103, may be positioned at any desired location in the housing 107, which may include locations proximate to edges 113, 115, or locations spaced from the edges 113, 115.

Figure 2A:
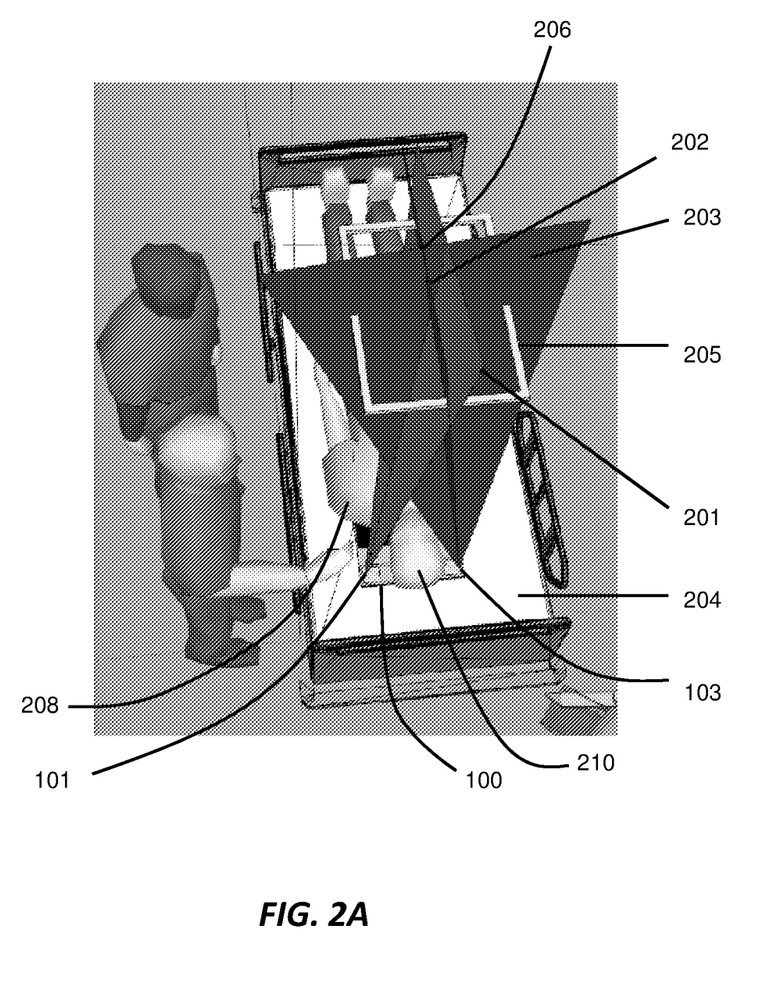
FIGS. 2A-2B depict perspective views for positioning of the detector alignment assembly of FIG. 1 and a laser sensor frame.
Figure 2B:
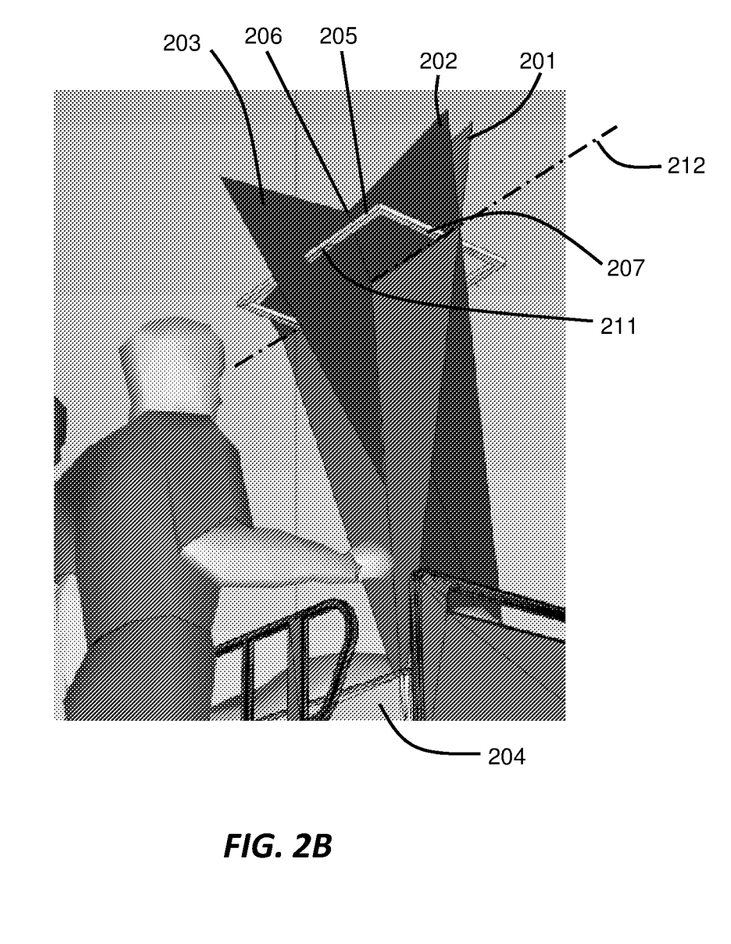

The planar laser beams just described are illustrated in the perspective view of FIGS. 2A and 2B. In one operational embodiment illustrated in the overhead perspective view of FIG. 2A, the detector assembly 100 may be placed on a bed 204 having a patient 208 lying thereon wherein at least the patient's head 210 may be positioned on the detector assembly 100 such that the laser modules 101, 103 are positioned on either side of the patient's head 210 and emit their respective planar laser beams upward in a direction away from the bed 204. As shown in FIGS. 2A and 2B, in one embodiment, the laser module 101 emits a single planar laser beam 201 upward away from the bed 204 at the same time that the laser module 103 emits two cross-wise planar laser beams 202, 203 upward away from the bed 204 such that the single planar laser beam 201 intersects both the cross-beams 202, 203 in a region above the bed 204. The laser module 103 may be configured to emit the two cross-wise planar laser beams 202, 203, in planes that intersect at a right angle or they may be configured to intersect at another desired angle. The intersection of the two cross-wise planar laser beams 202, 203, may be referred to as a cross line 206, or center of the cross-wise planar laser beams 202, 203, which is a line 206 extending from the laser module 103. The planar laser beam 201 emitted by the laser module 101 intersects the planar laser beam 202 emitted by the laser module 103 along a line 212 that is parallel to the linear dimension of lengthwise edges 113 of the detector assembly 100. The planar laser beams 201 and 202-203 may include a human-visible color difference, such as by using a green laser module for the laser module 101 and a red laser module for the laser module 103. The planar laser beams 201-203 emitted by each laser module 101, 103, may include a pulse frequency that is distinguishable as between the two laser modules, or the planar laser beams 201-203 may be distinguishable using other characteristics.

FIGS. 2A-2B each shows a rectangular, rigid, sensor frame 205, that contains four electronic sensors on a side of the frame 205 facing downward toward the bed 204. As described above, the frame 205 may be rigidly attached to an x-ray head, or an x-ray assembly, in a mobile radiographic imaging system. Two sensors 207, 211, are visible in the view of FIG. 2B. As shown in FIG. 2B, planar laser beams 201 and 202 intersect frame sensor 207 while planar laser beam 203 intersects frame sensor 211. These intersections of planar laser beams 201-203 with sensors in the frame 205 will be more fully described in relation to FIG. 4. With respect to FIG. 3, there is illustrated a top view of the detector assembly 100 and frame 205 showing the planar laser beams 201-203 being emitted by laser modules 101, 103, of the detector assembly 100 upward way from the bed 204 and the patient 208 toward the frame 205 which is positioned above the bed 204. The frame sensors of the frame 205 face the detector assembly 100 and are not visible in FIG. 3.

Figure 3:
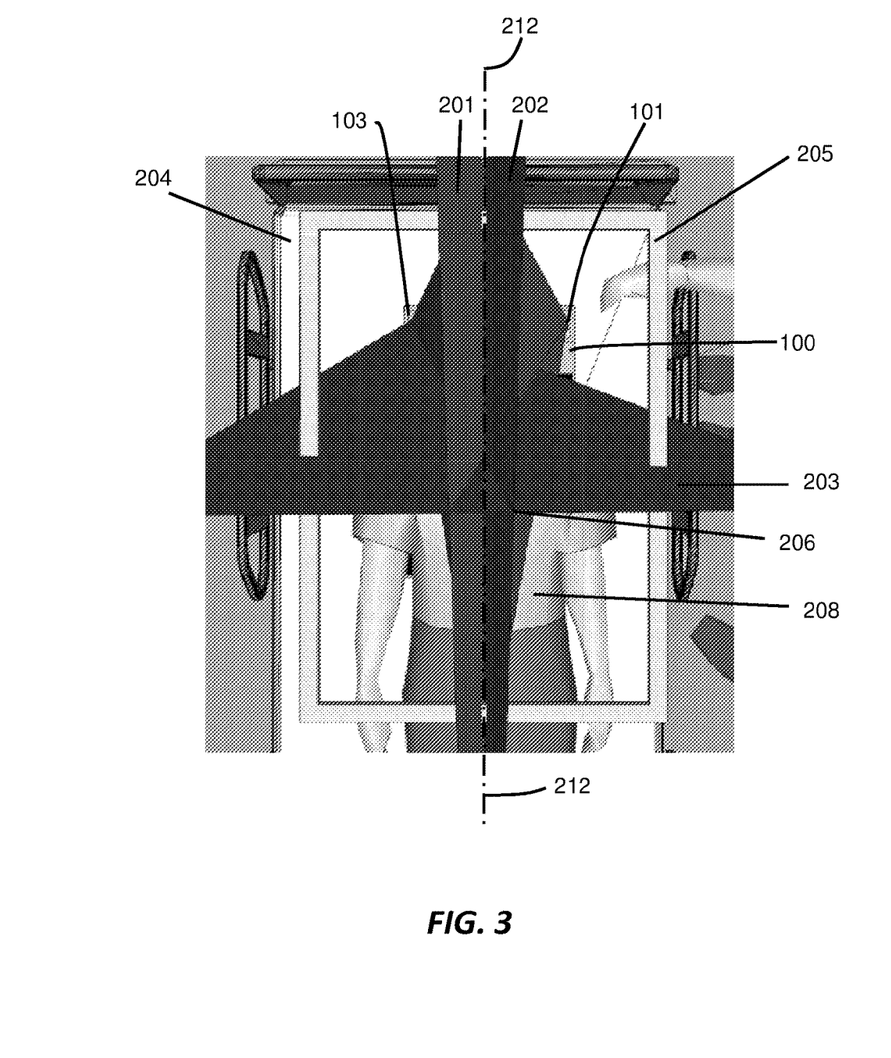
FIG. 3 is a top view of the perspective view of FIGS. 2A-2B.
Figure 4:
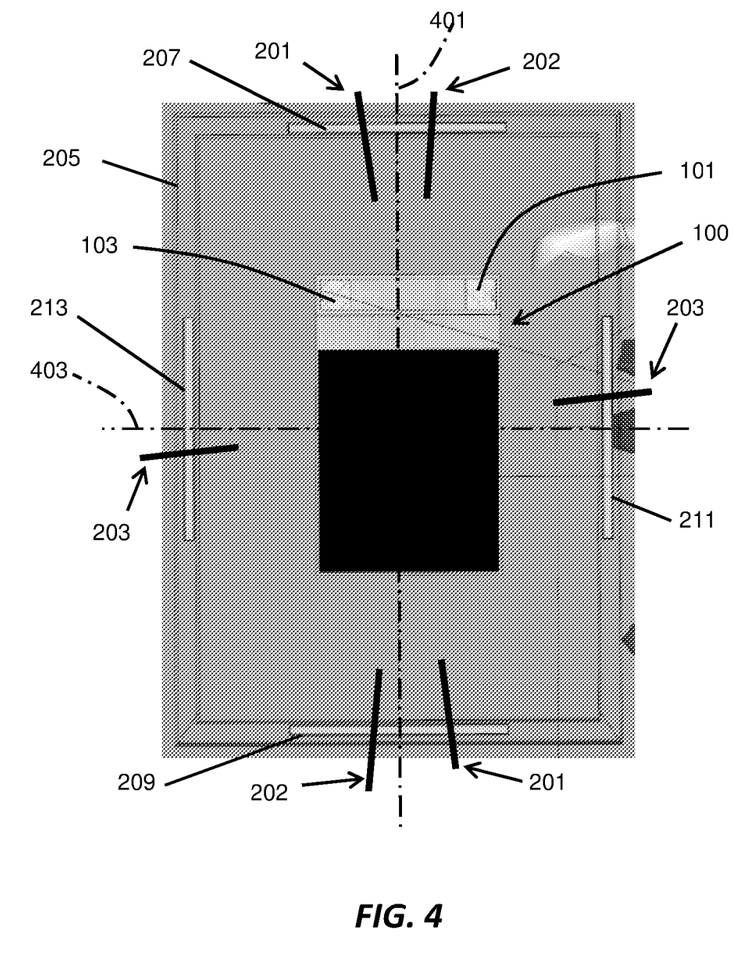
FIG. 4 is a schematic transparent view of FIG. 3.

With reference to FIG. 4 there is illustrated in schematic form the general geometric arrangement of the detector assembly 100 and frame 205 as shown in FIG. 3, but in transparent form and without the bed 204 and patient 208. The planar laser beams 201-203 are illustrated with only a portion of their linear dimensions that intersect electronic frame sensors 207, 209, 211, and 213. Thus, planar laser beam 201 emitted by laser module 101 is shown to intersect frame sensor 207 and frame sensor 209 in one, or a first, linear dimension, while planar laser beam 202 emitted by laser module 103 is shown to intersect frame sensor 207 and frame sensor 209 in another, or a second, linear dimension, while planar laser beam 203 emitted by laser module 103 is shown to intersect frame sensor 211 and frame sensor 213 in another, or a third, linear dimension. The planar laser beams 201-203 may be said to intersect the frame 205 along a length dimension of the planar laser beams 201-203, which planar laser length dimensions traverse a width and length of the frame 205. Although the frame 205 is illustrated as having a rectangular shape, the frame 205 may be formed in a circular configuration or another appropriate geometry. The frame 205 may not necessarily be formed in one unitary piece, but may include several individual sections each containing one or more of the frame sensors 207, 209, 211, and 213. Although shown in a symmetrical arrangement in FIG. 4, the frame sensors 207, 209, 211, and 213, may not necessarily be arranged symmetrically with respect to each other, with respect to a supporting frame, or with respect to the laser sources 101, 103. The frame sensors 207, 209, 211, and 213, may not necessarily be equidistant from either of the laser sources 101, 103, with respect to any particular dimension. The dimensions of the frame 205 may vary, from about a 4×4 or 3×5 inch frame up to about 30×30 inches. The frame sensors 207, 209, 211, and 213 may each be configured to detect and differentiate the planar laser beams 201-203 such as by detecting distinguishing characteristics of the planar laser beams 201-203. In one embodiment, the frame sensors 207, 209, 211, and 213 are configured to detect a color of each of the planar laser beams 201-203. In one embodiment, the frame sensors 207, 209, 211, and 213 are configured to detect a pulse frequency of each of the planar laser beams 201-203. Similarly, the laser source 101, 103, may be fabricated, or programmed, to emit pulsed laser beams at selected frequencies.

As shown in FIG. 4, the first, second, and third linear dimensions of the planar laser beams 201-203, respectively, as they may be detected by the frame sensors 207, 209, 211, and 213, are different and depend on the geometric relationship of the frame 205 with respect to the laser modules 101, 103, or, equally, they depend on the geometric relationship of the frame 205 with respect to the detector assembly 100. In the example of FIG. 4, the frame sensors 207, 209, 211, and 213, altogether may detect six points of intersection of the three linear dimensions of the planar laser beams 201-203, two points of intersection in each of frame sensors 207, 209, and one in each of frame sensors 211, 213. In one symmetrical embodiment, the lengthwise and widthwise central axes 401, 403, respectively, may be said to bisect the frame sensors 207, 209, 211, and 213, and the corresponding four edges of the rectangular sensor frame 205.

Figure 5A:
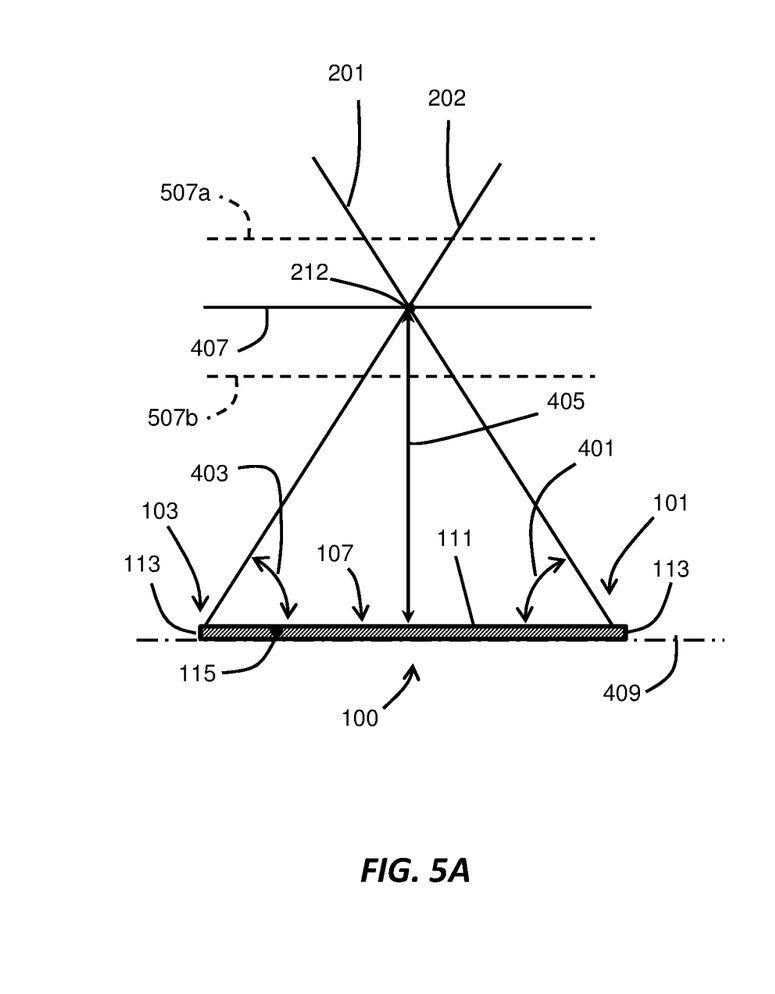
FIGS. 5A-5B are side views of the detector assembly.
Figure 5B:
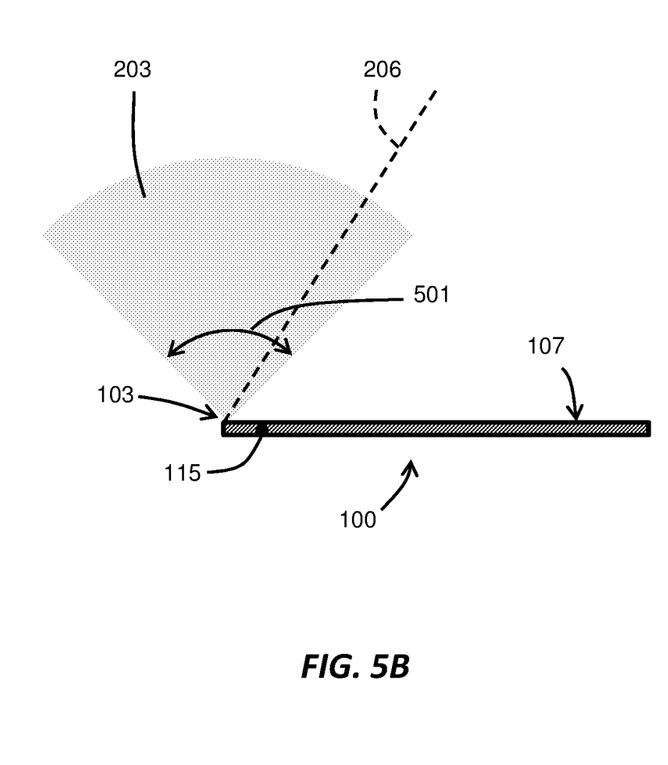

FIGS. 5A-5B illustrate a side view of the detector assembly 100 as seen from the widthwise bottom edge 115. In one embodiment, the laser module 101 is permanently affixed into the housing 107 to emit a single planar laser beam 201 in a direction such that the planar laser beam 201 intersects a plane 407 parallel to the plane 409 of the detector assembly 100 along a line (perpendicular to the page as seen in FIG. 5A) that is parallel to the linear dimension of either of the lengthwise edges 113 of the detector module 100. Similarly, in this embodiment, the laser module 103 is permanently affixed into the housing 107 to emit two cross-wise planar laser beams 202, 203 (planar laser beam 203 is illustrated only in FIG. 5B for clarity), in a direction such that one of the planar laser beams 202 intersects a plane 407 parallel to the plane 409 of the detector assembly 100 along a line that is parallel to the linear dimension of either of the lengthwise edges 113 of the detector module 100. Similarly, as described herein, the planar laser beam 201 emitted by the laser module 101 intersects the planar laser beam 202 emitted by the laser module 103 along an intersection line 212 that is parallel to the linear dimension of lengthwise edges 113 of the detector assembly 100.

At one particular distance 405 from a top surface 111 of the detector assembly 100, the intersection line 212 as between the plane 407 and the planar laser beams 201, 202, is collinear. In other exemplary planes 507a, 507b, parallel to the plane 409 of the detector assembly 100, at different distances from the top surface 111 of the detector assembly 100, the planar laser beams 201, 202, intersect these planes 507a, 507b, along parallel lines. In other exemplary planes (not shown) that are not parallel to the plane 409 of the detector assembly 100, the planar laser beams 201, 202, may intersect such planes along non-parallel lines, or one, or both, of the planar laser beams 201, 202, may not intersect such planes at all. The distance 405 of the line 212 from a top surface 111 of the detector assembly 100 is determined by the angles 401, 403, at which the laser modules 101, 103, respectively, are intentionally configured to be aimed. The angles 401, 403, may be preselected and the respective laser modules, 101, 103, may be permanently affixed at the preselected angles 401, 403, within the housing 107.

In one embodiment, the angles 401, 403, may be selected such that the distance 405 matches a desired source-to-image distance (SID) implemented in an x-ray imaging system that utilizes the detector assembly 100. Such SID may be selected to be anywhere between about two feet and about eight feet. The laser modules 101, 103, may be appropriately fixed in respective positions in the housing 107 of the detector assembly 100 to emit planar laser beams 201, 202, at the desired angles 401, 403, to achieve the desired SID. In one embodiment, if the frame 205 is appropriately positioned in the plane 407, the frame sensors 207, 209, 211, 213, will detect four distinct points of intersection, instead of the six points of intersection illustrated in FIG. 4, because the planar laser beams 201, 202, will be collinear at the sensor frame 205 in that position, and will precisely overlap in frame sensors 207, 209. However, because the planar laser beams 201, 202, may be distinguished by color or pulse frequency, using the electronic frame sensors 207, 209, as described herein, the electronic frame sensors 207, 209, may nonetheless individually detect four collinear overlapping signals from two separate planar laser beams 201, 202.

Turning to FIG. 5B, there is illustrated the same view of the detector assembly 100 as shown in FIG. 5A, showing an exemplary planar laser beam 203 pre-designed fan angle 501 of about 90° as emitted by the laser module 103. As explained above, the laser module 103 is permanently affixed into the housing 107 to emit two cross-wise planar laser beams 202, 203, in a direction such that one of the planar laser beams 203 intersects planar laser beam 202 at a right angle, or another selected angle, along a line 206 that extends from the laser module 103. Although only one exemplary fan angle 501 of the planar laser beam 203 is illustrated, both laser modules 101, 103, may emit planar laser beams 201-203 having equivalent preselected fan angles as desired. Laser modules 101, 103, may be configured to emit planar laser beams 201-203 having fan angles 30°, 45°, or any other desired fan angle. The fan angles may be equivalent as between the laser modules 101, 103, or they may be configured differently. The fan angles may be fixed at manufacture or they may be adjustable in the field. Similarly, the installation of laser modules 101, 103, may be permanently affixed at the preselected angles 401, 403, within the housing 107, or the angles 401, 403, may be variable in the field by mechanically adjusting a position of the modules 101, 103, and may require periodic calibration. Although planar laser beams 201-203 are illustrated in the figures as having a terminal ends in space, persons having ordinary skill in the art will understand that the planar laser beams 201-203 propagate through space indefinitely.

Figure 6:
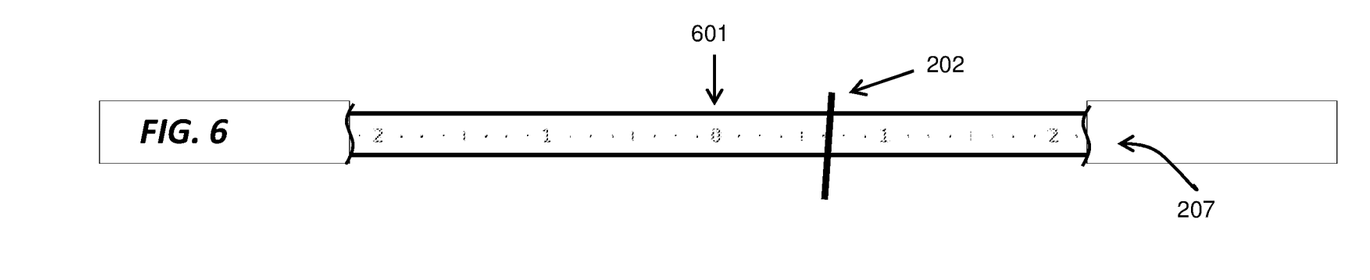
FIG. 6 illustrates an exemplary frame sensor.
Figure 7:
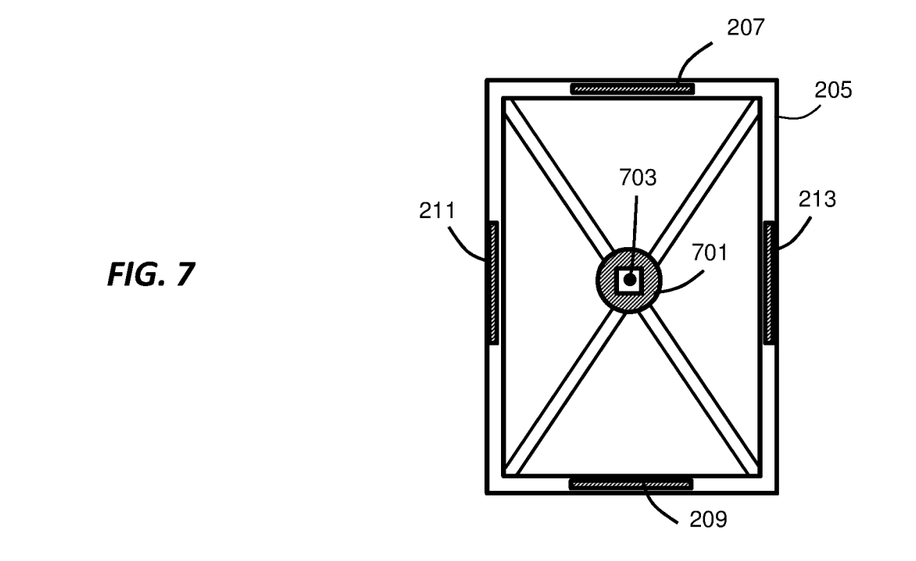
FIG. 7 illustrates an exemplary detector alignment system.

With reference to FIG. 6, there is depicted an exemplary embodiment of one of the frame sensors 207, 209, 211, 213, namely, the frame sensor 207 as shown in FIG. 4 wherein the planar laser beam 202 impacts the frame sensor 207. The frame sensors 207, 209, 211, 213 may each include a linear, or two dimensional, array of photosensors to detect a laser beam, and be calibrated to detect and store a digital value representing an intersection point in the frame sensor 207, 209, 211, 213, where the linear dimension of the planar laser beam 201-203 impacts the frame sensor 207, 209, 211, 213. FIG. 6 illustrates frame sensor 207 as having a visible zero centered numerical calibration scale for illustrative purposes. The zero point 601 of the exemplary scale may represent a center of the frame sensor 207 that coincides with a bisecting axis 401 of the frame 205, for example. In an actual operative embodiment, the frame sensors 207, 209, 211, 213, may not include a visible measurement scale, but may be logically demarcated using programmed electronics to measure a signal intensity detected by each of the photosensors in the array and to identify a location along a length of the frame sensor 207, 209, 211, 213, of the photosensor that receives the greatest laser intensity. In one embodiment, a location of the planar laser beam intersection point along a length of the frame sensor 207, 209, 211, 213, may be determined by detecting peak laser intensity. In one embodiment, a location of the planar laser beam intersection point along a length of the frame sensor 207, 209, 211, 213, may be determined by using a plurality of adjacent photosensors that detect the planar laser beam, i.e., are impacted by photons of the planar laser beam. By logically combining and calculating the detected readings as between complementary frame sensors 207, 209, and 211, 213, on opposite edges of the frame 205, as illustrated in FIG. 4, e.g., up to six intersection points detected by the frame sensors, the linear dimensions of the planar laser beams 201-203, can be identified and located with respect to the frame 205. As illustrated in FIG. 7, a sensor frame 205, having frame sensors 207, 209, 211, 213, may be attached to an x-ray source 701 so that the x-ray source 701 is positioned substantially in a center of the sensor frame 205, or in another preselected position, such that a central ray 703 of an x-ray beam emitted (out of the page as depicted in FIG. 7) by the x-ray source 701 is generally perpendicular to a plane of the sensor frame 205. In this configuration, in combination with the DR detector assembly 100 disclosed herein, there is provided a DR detector and x-ray source alignment system that detects parallel and non parallel alignment of a DR detector assembly 100 with the x-ray source attached sensor frame 205.

The system as described herein may be implemented with low cost, small, light weight components, such as laser beam diodes or modules emitting lines and/or crosses, and long linear sensors implemented as CMOS contact image sensor (CIS) arrays or charge coupled device (CCD) arrays with reducing optics. A SELFOC lens array as used in CIS arrays may be used. These are sensors that have been developed for document image scanning. The system may be implemented without any tethering or communication between the laser modules and the frame sensors, which allows the system to be retrofitted to existing radiographic imaging facilities. The system may include a direct optical path between the laser beam modules and the frame sensors, which optical path may be asymmetric. The frame and frame sensors can be placed on an x-ray head. Larger spacing there provides higher sensing accuracy. The components may be low power components such as laser diodes, contact image sensors, and PCB based controllers. The laser modules may be attachable and detachable from a reusable object, such as a detector housing, which allows for easy replacement if one is broken. It also allows for laser diodes with different configurations to be used. In one embodiment, laser diode mounts may be configured such that the laser sources are positioned at raised points at a selected distance from a top surface of the DR detector.

As described herein, the features of the present invention are disclosed as exemplary embodiments. The laser modules include two laser modules emitting a cross-wise planar beam and one planar beam producing one dimensional beams or lines having a total of three planes/lines through space. Four color sensing frame sensors, or line sensor segments, are disclosed upon which the intersection positions of the planar laser beams thereon are detected and measured. The association between the sensed intersection points and which laser module generated the sensed light may thus be determined. In one embodiment, intersecting planar laser beams forming a cross of one color (red) may be used together with a planar laser beam shaped as a line of another color (green). The cross-wise pattern may be implemented as two lines, such as from two separate laser modules. The color sensing linear frame sensors may be used and so the association as to the correct laser module may be made.

In one embodiment, monochrome sensors may be used having color filters placed thereon, such as green and red color filters. In this embodiment, six monochromatic sensors may be used (two each for frame sensors wherein the planar laser beams from both modules may impact it) to allow color sensing to associate the sensed intersection point and light source. More light sources and more sensors may be added to either extend the range of sensing (to handle larger angles and larger displacements) or to provide more accurate measurement. A diffusion filter may be placed in front of the sensors to optimize the light detected by the sensor such as when SELFOC lenses are used in a CIS module. The association between the laser source and the detector may also be established (as an alternative to color separation) by pulsing the laser source at a particular frequency or through other means of encoding and/or communication between the light source and detection systems. The system can be implemented with placement of the light sources and frame sensors to meet the free optical path requirements for any given measurement problem. The light sources may be chosen to not interfere with other attributes of a system (e.g., they could be different infrared wavelengths so as to not interfere with a visible light system). In a radiographic imaging system the light probably would not interfere with any other operational component of the system. The placement of light sources and the length and position sensing accuracy of the frame sensors can be selected to meet the needs of a given application for both sensing accuracy and range of operation (displacement amount and orientation allowance). For example, A4 sized frame sensors are 216 mm long. Components of other lengths exist, for example, A3 sensors are typically 305 mm long. The use of linear sensing arrays provides for high accuracy of light position detection over large angular ranges. Frame sensors may measure light line intersection accuracy from about 200 to about 1200 dpi, which provides positioning information within about 21.2-127 microns. A CIS array can be read out in a time on the order of 1 ms. This allows measurements to be made quickly. Another option for a frame sensor to measure the intersection points of the planar laser beams is with a linear sensor having contact image sensors which are used in flatbed scanners. If the illumination source was disabled or removed, and a filament like object was placed along the length of the sensor along the focal line it would intersect the light and the light would be detected by the sensor to measure the intersection point. U.S. Pat. No. 5,729,475, entitled "Optical System for Accurate Monitoring of the Position and Orientation of an Object" describes an approach of imaging four or more LEDs using a specific 3D arrangement and using camera sensed (imaged) locations. The laser modules described herein may include a Red Laser Cross Line Module and a Uniform Green Laser Line Module as made by World Star Tech, of Markham, ON, Canada; and the frame sensor may include a three color CCD linear image sensor made by NEC Corporation of America, of Irving, Tex.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A digital radiographic detector apparatus comprising:
   a front surface configured to detect x-ray radiation;
   a first source of electromagnetic radiation configured to project a first planar beam in a direction away from the front surface, the first planar beam detectable along a first linear dimension; and
   a second source of electromagnetic radiation configured to project a second planar beam in a direction away from the front surface, the second planar beam detectable along a second linear dimension,
   wherein the second source of electromagnetic radiation is further configured to project a third planar beam in a direction away from the front surface, the third planar beam detectable along a third linear dimension, and
   wherein the first and second sources are configured such that the first, second and third planar beams are detectable between about one foot and about ten feet from the apparatus using a planar beam sensor assembly, the planar beam sensor assembly comprising a plurality of sensors for determining at least two points in each of the first, second and third linear dimensions.

2. The apparatus of claim 1, wherein the second and third planar beams are perpendicular.

3. The apparatus of claim 1, wherein the first and second sources are configured such that the first linear dimension and the second linear dimension are detectible as parallel lines.

4. The apparatus of claim 1, wherein the first and second sources are configured such that the first linear dimension and the second linear dimension are detectible as collinear.

5. The apparatus of claim 4, wherein the first and second sources are configured such that the third linear dimension is detectible as being perpendicular to both the first and second linear dimensions.

6. The apparatus of claim 1, wherein the first and second sources comprise laser beam sources.

7. The apparatus of claim 1, wherein the first source of electromagnetic radiation is configured to project the first planar beam having a first detectible characteristic, and wherein the second source of electromagnetic radiation is configured to project the second planar beam having a second detectible characteristic different from the first detectible characteristic.

8. The apparatus of claim 7, wherein the first and second detectible characteristics are selected from the group consisting of wavelength and pulse frequency.

9. The apparatus of claim 1, wherein the front surface comprises a two dimensional array of imaging sensors configured to capture a radiographic image.

10. The apparatus of claim 1, wherein the first and second sources are configured such that the first linear dimension and the second linear dimension are detectible as parallel or collinear by the planar beam sensor assembly when the planar beam sensor assembly is disposed in a plane that is parallel to a plane in which the digital radiographic detector is disposed.

11. A method comprising:
    emitting a planar laser beam from a first laser source;
    emitting two cross-wise planar laser beams from a second laser source;
    detecting relative positions of the planar laser beam and the two cross-wise planar laser beams using a plurality of electronic sensors positioned between about one foot and about ten feet from the first and second laser sources, the plurality of electronic sensors each comprising a linear array of photosensors; and
    determining a parallel and non-parallel position of the detector with respect to the first and second laser sources based on the relative positions of the planar laser beam and the two cross-wise planar laser beams.

12. The method of claim 11, further comprising attaching the plurality of electronic sensors to an x-ray source in a fixed spatial relationship thereto.

13. The method of claim 11, further comprising detecting at least two points of intersection as between the first planar laser beam and the plurality of electronic sensors.

14. The method of claim 11, further comprising detecting at least two points of intersection as between each of the two cross-wise planar laser beams and the plurality of electronic sensors.

15. A positioning system for radiographic imaging, the system comprising:
    a planar two dimensional array of imaging sensors configured to capture a radiographic image;
    a first source of electromagnetic radiation configured to project a first planar beam in a direction away from the array of imaging sensors;
    a second source of electromagnetic radiation configured to project two perpendicular cross-wise planar beams in a direction away from the array of imaging sensors; and
    a plurality of electronic sensors disposed to intersect the first planar beam and the two perpendicular cross-wise planar beams, wherein the plurality of electronic sensors each comprise photosensors configured to detect two points of intersection for the first planar beam and for each of the two cross-wise planar beams.

16. The apparatus of claim 15, wherein the plurality of electronic sensors are disposed in one common plane.

17. The apparatus of claim 15, wherein the plurality of electronic sensors are attached in a fixed spatial relationship to an x-ray source.

* * * * *